US008792704B2

(12) United States Patent
Isaacs

(10) Patent No.: US 8,792,704 B2
(45) Date of Patent: *Jul. 29, 2014

(54) IMAGING SYSTEM AND METHOD FOR USE IN SURGICAL AND INTERVENTIONAL MEDICAL PROCEDURES

(71) Applicant: Robert E. Isaacs, Chapel Hill, NC (US)

(72) Inventor: Robert E. Isaacs, Chapel Hill, NC (US)

(73) Assignee: SafeRay Spine LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/011,344

(22) Filed: Aug. 27, 2013

(65) Prior Publication Data
US 2013/0342578 A1 Dec. 26, 2013

Related U.S. Application Data

(63) Continuation of application No. 13/253,838, filed on Oct. 5, 2011, now Pat. No. 8,526,700.

(60) Provisional application No. 61/390,488, filed on Oct. 6, 2010.

(51) Int. Cl.
G06K 9/00 (2006.01)
G06F 19/00 (2011.01)
G06T 7/00 (2006.01)
G01N 23/04 (2006.01)

(52) U.S. Cl.
CPC .......... G06T 7/0024 (2013.01); G06F 19/3443 (2013.01); G06F 19/3481 (2013.01); G06F 19/321 (2013.01)
USPC .............................. 382/133; 382/274; 378/62

(58) Field of Classification Search
USPC ......... 382/100, 103, 128–134, 153–155, 162, 382/168, 173, 181, 219, 232, 254, 255, 274, 382/276, 285, 305, 312; 600/426, 424; 378/4, 21, 62, 204
See application file for complete search history.

(56) References Cited

U.S. PATENT DOCUMENTS 4,367,490 A 1/1983 Riederer
4,641,352 A 2/1987 Fenster et al.
(Continued)

OTHER PUBLICATIONS

Metz, C.T. et al. "GPU Accelerated Alignment of 3-D CTA with 2-D X-Ray Data for Improved Guidance in Coronary Interventions," IEEE 2009, pp. 959-962.
(Continued)

Primary Examiner — Seyed Azarian
(74) Attorney, Agent, or Firm — Maginot, Moore & Beck, LLPsA

(57) ABSTRACT

A system and method for displaying images of internal anatomy includes an image processing device configured to provide high resolution images of the surgical field from low resolution scans during the procedure. The image processing device digitally manipulates a previously-obtained high resolution baseline image to produce many representative images based on permutations of movement of the baseline image. During the procedure a representative image is selected having an acceptable degree of correlation to the new low resolution image. The selected representative image and the new image are merged to provide a higher resolution image of the surgical field. The image processing device is also configured to provide interactive movement of the displayed image based on movement of the imaging device, and to permit placement of annotations on the displayed image to facilitate communication between the radiology technician and the surgeon.

24 Claims, 10 Drawing Sheets

(56) References Cited

U.S. PATENT DOCUMENTS

| | | | |
|---|---|---|---|
| 5,195,234 A | 3/1993 | Pine et al. | |
| 5,211,165 A | 5/1993 | Dumoulin et al. | |
| 5,253,169 A | 10/1993 | Corby, Jr. | |
| 5,396,531 A | 3/1995 | Hartley | |
| 5,467,380 A | 11/1995 | De Jonge et al. | |
| 5,676,673 A | 10/1997 | Ferre et al. | |
| 5,772,594 A | 6/1998 | Barrick | |
| 5,901,199 A | 5/1999 | Murphy et al. | |
| 5,911,012 A | 6/1999 | Bernard et al. | |
| 5,951,475 A | 9/1999 | Gueziec et al. | |
| 6,125,164 A | 9/2000 | Murphy et al. | |
| 6,215,848 B1 | 4/2001 | Linders et al. | |
| 6,236,875 B1 | 5/2001 | Bucholz et al. | |
| 6,256,403 B1 | 7/2001 | Florent et al. | |
| 6,314,160 B1 | 11/2001 | Dhawale et al. | |
| 6,330,356 B1 | 12/2001 | Sundareswaran et al. | |
| 6,381,352 B1 | 4/2002 | Nelson | |
| 6,463,121 B1 | 10/2002 | Milnes | |
| 6,477,400 B1 | 11/2002 | Barrick | |
| 6,775,405 B1 | 8/2004 | Zhu | |
| 6,990,368 B2 | 1/2006 | Simon et al. | |
| 7,054,474 B1 | 5/2006 | Krieger | |
| 7,194,117 B2 | 3/2007 | Kaufman et al. | |
| 7,204,640 B2 | 4/2007 | Fu et al. | |
| 7,274,771 B2 | 9/2007 | Allred et al. | |
| 7,317,841 B2 | 1/2008 | Yatsenko et al. | |
| 7,324,678 B2 | 1/2008 | Allouche | |
| 7,404,673 B2 | 7/2008 | Hörnig | |
| 7,505,617 B2 | 3/2009 | Fu et al. | |
| 7,526,065 B2 * | 4/2009 | Hardesty | 378/62 |
| 7,599,575 B2 * | 10/2009 | Lienard et al. | 382/274 |
| 7,603,155 B2 | 10/2009 | Jensen | |
| 7,658,541 B2 * | 2/2010 | Li et al. | 378/204 |
| 7,672,709 B2 | 3/2010 | Lavallee et al. | |
| 7,817,834 B2 | 10/2010 | Bernhardt et al. | |
| 7,848,592 B2 | 12/2010 | Chen et al. | |
| 7,853,305 B2 * | 12/2010 | Simon et al. | 600/424 |
| 7,856,130 B2 | 12/2010 | Suri et al. | |
| 7,885,441 B2 * | 2/2011 | Node-Langlois et al. | 382/128 |
| 2005/0047544 A1 | 3/2005 | Fu et al. | |
| 2005/0272991 A1 | 12/2005 | Xu et al. | |
| 2006/0002630 A1 | 1/2006 | Fu et al. | |
| 2006/0116575 A1 | 6/2006 | Willis | |
| 2006/0293592 A1 | 12/2006 | Jensen | |
| 2007/0189603 A1 | 8/2007 | Kasperkiewicz et al. | |
| 2008/0269602 A1 * | 10/2008 | Csavoy et al. | 600/426 |
| 2009/0324041 A1 | 12/2009 | Narayanan et al. | |
| 2009/0326363 A1 | 12/2009 | Li et al. | |
| 2010/0001996 A1 | 1/2010 | Shen et al. | |
| 2010/0004526 A1 | 1/2010 | Wei et al. | |
| 2010/0004530 A1 | 1/2010 | Kumar et al. | |
| 2010/0207942 A1 | 8/2010 | Zhao | |
| 2011/0152676 A1 | 6/2011 | Groszmann et al. | |

OTHER PUBLICATIONS

Gong, Ren Hui and Abolmaesumi, Purang, "2D/3D Registration with the CMA-ES Method," Proceedings of SPIE, vol. 6918, 69181M, 2008.

Cheryauka, Arvi, Barrett, Johnny and Wang, Zhonghua, "3-D Geometry Calibration and Markerless Electromagnetic Tracking with a Mobile C-arm," Proceedings of SPIE, vol. 6509, 650927-1, 2007.

West, Jay B. and Maurer, Calvin R., Jr., "A System for Finding a 3D Target Without a 3D Image," Proceedings of SPIE, vol. 6918 69180J-1, 2008.

Wilson, Emmanuel, Yaniv, Ziv, Lindisch, David and Cleary, Kevin, "A Buyer's Guide to Electromagnetic Tracking System for Clinical Applications," Proceedings of SPIE, vol. 6918, 69182B-1, 2008.

Koishi, Takeshi, et al., "A Navigation System Using Projection Images of Laparoscopic Instruments and a Surgical Target with Improved Image Quality," Proceedings of SPIE, vol. 6918, 69181O-1, 2008.

Kwartowitz, David M., et al, "A Novel Technique for Analysis of Accuracy of Magnetic Tracking Systems Used in Image Guided Surgery," Proceedings of SPIE, vol. 7625 76251L-1, 2010.

Ding, Jienan, et al., "Accuracy Analysis of an Image-Guided System for Vertebroplasty Spinal Therapy Based on Electromagnetic Tracking of Instruments," Proceedings of SPIE, vol. 6918 69181K-1, 2008.

Brost, Alexander, et al., "Accuracy of X-Ray Image-Based 3D Localization from Two C-Arm Views: A Comparison Between an Ideal System and a Real Device," Proceedings of SPIE, vol. 7261 72611Z-1, 2009.

Jomier, Julien, et al., "An Open-Source Framework for Testing Tracking Devices Using Lego Mindstorms," Proceedings of SPIE, vol. 7261 72612S-1, 2009.

Foroughi, Pezhman, Taylor, Russell H. and Fichtinger, Gabor, "Automatic Initialization of 3D Bone Registration," Proceedings of SPIE, vol. 6918, 69182P-1, 2008.

Jain, Ameet Kumar, et al., "C-arm Calibration—is it Really Necessary?" Proceedings of SPIE, vol. 6509 65092U-1, 2007.

Mori, Kensaku, et al., "Compensation of Electromagnetic Tracking System Using an Optical Tracker and its Application to Bronchoscopy Navigation System," Proceedings of SPIE, vol. 6509 65090M-1, 2007.

Hagedorn, John G., et al., "Correction of Location and Orientation Errors in Electromagnetic Motion Tracking," Presence, vol. 16, No. 4, Aug. 2007, pp. 352-366.

Lu, J., Egger, J., Wimmer, A., Grobkoph, S. and Freisleben, B., "Detection and Visualization of Endoleaks in CT Data for Monitoring of Thoracic and Abdominal Aortic Aneurysm Stents," Proceedings of SPIE, vol. 6918 69181 F-1, 2008.

Schneider, Mark and Stevens, Charles, "Development and Testing of a New Magnetic-Tracking Device for Image Guidelines," Proceedings of SPIE, vol. 6509 650901-1, 2007.

Röbler, Friedmann, et al., "Distributed Video Generation on a GPU-Cluster for the Web-Based Analysis of Medical Image Data," Proceedings of SPIE, vol. 6509 650903-1, 2007.

Shen, Eric, et al., "Effects of Sensor Orientation on AC Electromagnetic Tracking System Accuracy in a CT Scanner Environment," Proceedings of SPIE, vol. 6918 691823-1, 2008.

Nagel, Markus, et al., "Electromagnetic Tracking System for Minimal Invasive Interventions Using a C-Arm System With CT Options: First Clinical Results," Proceedings of SPIE, vol. 6918 69180G-1, 2008.

Hummel, Johann, et al., "Evaluation of Dynamic Electromagnetic Tracking Deviation," Proceedings of SPIE, vol. 7261 72612U-1, 2009.

Seslija, Petar, et al., "Feasibility of 3D Tracking of Surgical Tools Using 2D Single Plane X-Ray Projections," Proceedings of SPIE, vol. 6918 69180K-1, 2008.

Fitzpatrick, J. Michael, "Fiducial Registration Error and Target Registration Error Are Uncorrelated," Proceedings of SPIE, Vo. 7261 726102-1, 2009.

Chung, Adrian, J., et al., "Freehand Cocalibration of Optical and Electromagnetic Trackers for Navigated Bronchoscopy," LNCS 3150, pp. 320-328, 2004.

Siewerdsen, J.H., et al., "High-Performance Intraoperative Cone-Beam CT on a Mobile C-Arm: An Integrated System for Guidance of Head and Neck Surgery," Proceedings of SPIE, vol. 7261 72610J-1, 2009.

McDonald, Colin P., et al., "Implant Alignment in Total Elbow Arthroplasty: Conventional vs. Navigated Techniques," Proceedings of SPIE, vol. 7261 726112-1, 2009.

Liao, Rui, Xu, Ning, Sun, Yiyong, "Location Constraint Based 2D-3D Registration of Fluoroscopic Images and CT Volumes for Image-Guided EP Procedures," Proceedings of SPIE, vol. 6918 69182T-1, 2008.

Moghari, Mendi Hedjazi and Abolmaesumi, Purang, "Maximum Likelihood Estimation of the Distribution of Target Registration Error," Proceedings of SPIE, vol. 6918 691801-1, 2008.

Albers, Rob, Suijs, Eric and deWith, Peter H. N., "Memory-Efficient 3D Multi-Resolution Image Enhancement and Processing to Increase Throughput," Proceedings of SPIE, vol. 6918 69182Y-1, 2008.

(56) References Cited

OTHER PUBLICATIONS

Nafis, Christopher, Jensen, Vern and Von Jako, Ron, "Method for Evaluating Compatibility of Commercial Electromagnetic (EM) Micro Sensor Tracking Systems With Surgical and Imaging Tables" General Electric, (No Date).

Nagel, Markus, et al., "Needle and Catheter Navigation Using Electromagnetic Tracking for Computer-Assisted C-Arm CT Intervention," Proceedings of SPIE, vol. 6509 65090J-1, 2007.

Kindratenko, Volodymry and Sherman, William R., "Neural Network-Based Calibration of Electromagnetic Tracking System," Virtual Reality, 2006, 9, pp. 70-78.

Lin, Ralph, et al., "Phantom Evaluation of an Image-Guided Navigation System Based on Electromagnetic Tracking and Open Source Software," Proceedings of SPIE, vol. 6918 691826-1, 2008.

Shen, Eric, et al., "Quantification of AC Electromagnetic Tracking System Accuracy in a CT Scanner Environment," Proceedings of SPIE, vol. 6509 65090L-1, 2007.

Wörz, S., et al., "Quantification of the Aortic Arch Morphology in 3D CTA Images for Endovascular Aortic Repair (EVAR)," Proceedings of SPIE, vol. 6918 69181H-1, 2008.

Zagorchev, Lyubomir, et al., "Rapid Fusion of 2D X-Ray Fluoroscopy with 3D Multislice CT for Image-Guided Electrophysiology Procedures," Proceedings of SPIE, vol. 6509 65092B-1, 2007.

Kirsch, Stefan R., et al., "Assessment of Metallic Distortions of an Electromagnetic Tracking System," Proceedings of SPIE, vol. 6141, 61410J, 2006.

Yaniv, Ziv and Cleary, Kevin, "Fluoroscopy Based Accuracy Assessment of Electromagnetic Tracking," Proceedings of SPIE, vol. 6141, 61410L, 2006.

Kindratenko, Volodymyr V., "A Survey of Electromagnetic Position Tracker Calibration Techniques," Virtual Reality: Research, Development and Applications, 2000, vol. 5, No. 3, pp. 169-182.

Schaller, Christian, et al., "Time-of-Flight Sensor for Patient Positioning," Proceedings of SPIE, vol. 7261 726110-1, 2009.

Spiegel, Martin, et al., "Towards Real-Tim Guidewire Detection and Tracking in the Field of Neuroradiology," Proceedings of SPIE, vol. 7261 726105-1, 2009.

Ikits, Milan, et al., "An Improved Calibration Framework for Electromagnetic Tracking Devices," Scientific Computing and Imaging Institute, School of Computing University of Utah.

Murphy et al., "The Management of Imaging Dose During Image-Guided Radiotherapy," Medical Physics, vol. 34, No. 10, Oct. 2007 (pp. 4041-4063).

Metz, C.T., "Digitally Reconstructed Radiographs," Sep. 13, 2005, http://bigr.nl/files/publications/321_DRR.pdf. (83 pages).

International Search Report corresponding to PCT/US12/58845, dated Feb. 26, 2013 (13 pages).

* cited by examiner

Fig. 2A Full Dose
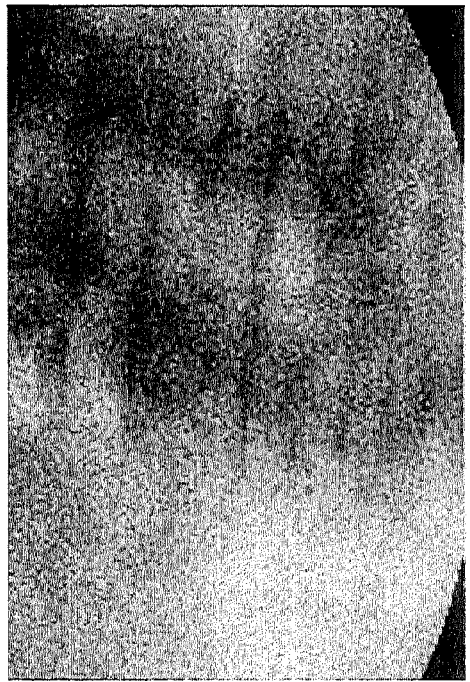
Fig. 2B Pulsed Low Dose
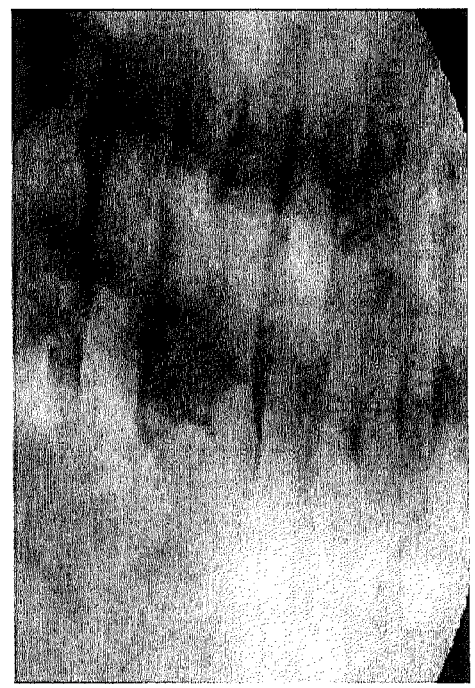
Fig. 2C

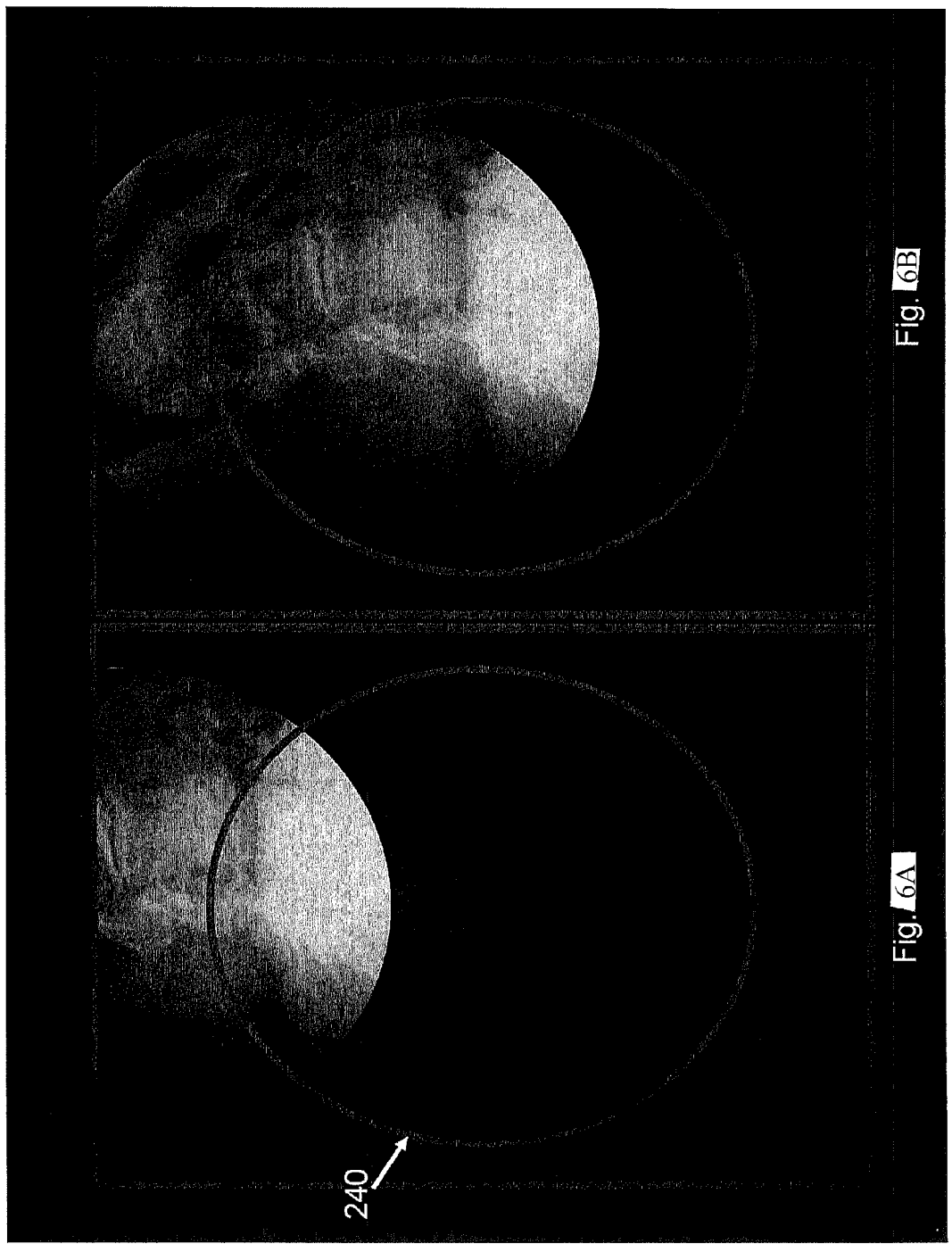

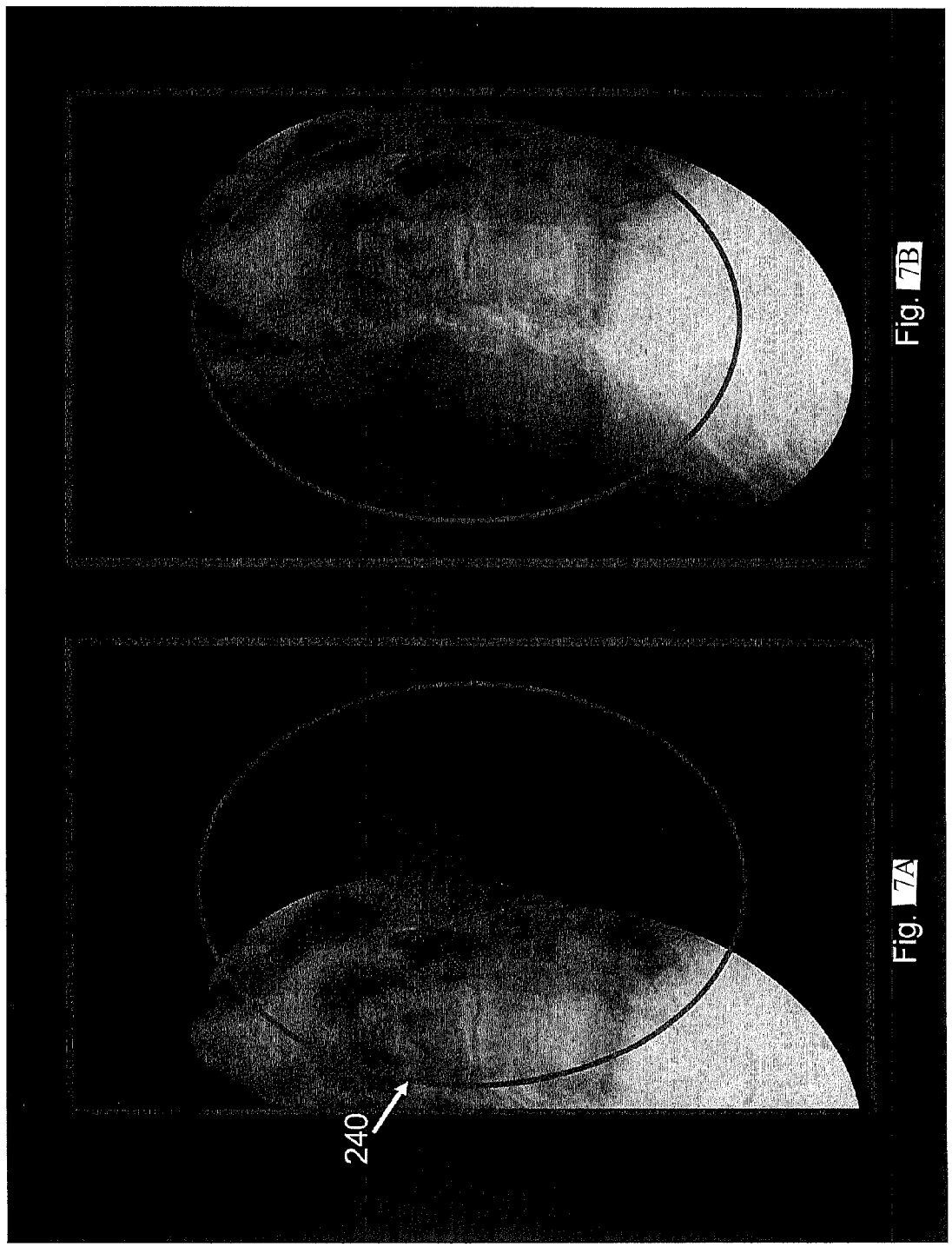

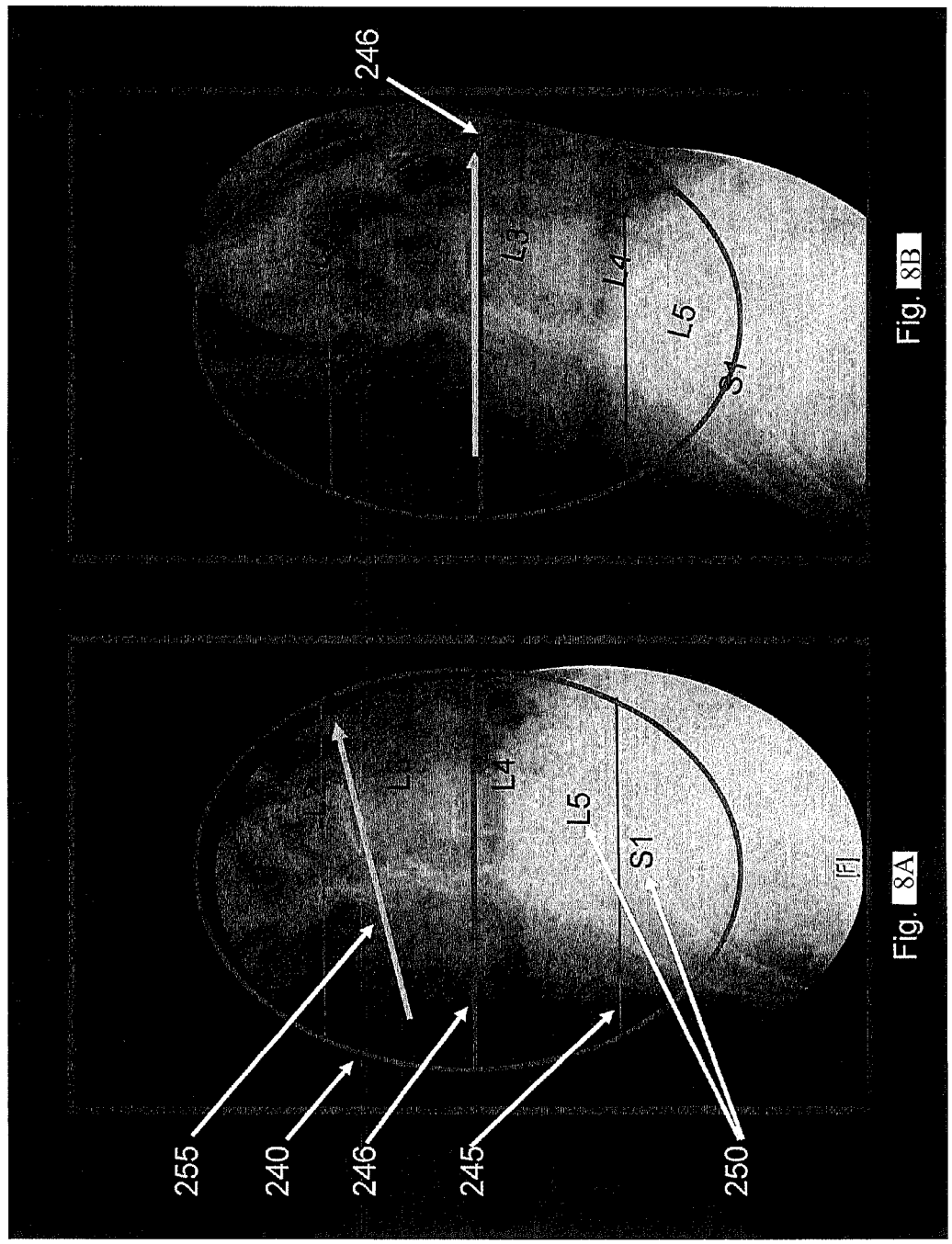

IMAGING SYSTEM AND METHOD FOR USE IN SURGICAL AND INTERVENTIONAL MEDICAL PROCEDURES

CROSS-REFERENCE TO RELATED APPLICATION

This application claims priority to and is a continuation of U.S. utility patent application Ser. No. 13/253,838, filed on Oct. 5, 2011, which issued on Sep. 3, 2013, as U.S. Pat. No. 8,526,700, and which claims priority to provisional application No. 61/390,488, filed on Oct. 6, 2010, and incorporates the entire disclosure herein by reference.

BACKGROUND

The present invention contemplates a system and method for altering the way a patient image, such as by X-ray, is viewed and obtained. More particularly, the inventive system and method provides means for decreasing the overall radiation to which a patient is exposed during a surgical procedure but without significantly sacrificing the quality or resolution of the image obtained.

Many surgical procedures require obtaining an image of the patient's internal body structure, such as organs and bones. In some procedures, the surgery is accomplished with the assistance of periodic images of the surgical site. Surgery can broadly mean any invasive testing or intervention performed by medical personnel, such as surgeons, interventional radiologists, cardiologists, pain management physicians, and the like. In surgeries and interventions that are in effect guided by serial imaging, which we will refer to as image guided, frequent patient images are necessary for the physician's proper placement of surgical instruments, be they catheters, needles, instruments or implants, or performance of certain medical procedures. Fluoroscopy, or fluoro, is one form of intraoperative X-ray and is taken by a fluoro unit, also known as a C-arm. The C-arm sends X-ray beams through a patient and takes a picture of the anatomy in that area, such as skeletal and vascular structure. It is, like any picture, a two-dimensional (2D) image of a three-dimensional (3D) space. However, like any picture taken with a camera, key 3D info may be present in the 2D image based on what is in front of what and how big one thing is relative to another.

A DRR is a digital representation of an X-ray made by taking a CT scan of a patient and simulating taking X-rays from different angles and distances. The result is that any possible X-ray that can be taken for that patient can be simulated, which is unique and specific to how the patient's anatomical features look relative to one another. Because the "scene" is controlled, namely by controlling the virtual location of a C-Arm to the patient and the angle relative to one another, a picture can be generated that should look like any X-ray taken in the operating room (OR).

Many imaging approaches, such as taking fluoro images, involve exposing the patient to radiation, albeit in small doses. However, in these image guided procedures, the number of small doses adds up so that the total radiation exposure can be problematic not only to the patient but also to the surgeon or radiologist and others participating in the surgical procedure. There are various known ways to decrease the amount of radiation exposure for a patient/surgeon when an image is taken, but these approaches come at the cost of decreasing the resolution of the image being obtained. For example, certain approaches use pulsed imaging as opposed to standard imaging, while other approaches involve manually altering the exposure time or intensity. Narrowing the field of view can potentially also decrease the area of radiation exposure and its quantity (as well as alter the amount of radiation "scatter") but again at the cost of lessening the information available to the surgeon when making a medical decision. Further, often times images taken during a surgical intervention are blocked either by extraneous OR equipment or the actual instruments/implants used to perform the intervention. Limiting the blocking of the normal anatomy behind those objects would have tangible benefits to the medical community.

There is a need for a an imaging system, that can be used in connection with standard medical procedures, that reduces the radiation exposure to the patient and medical personnel, but without any sacrifice in accuracy and resolution of an X-ray image. There is also a need for an imaging system that accounts for instruments and hardware, such as implants, that might otherwise obscure a full view of the surgical site.

SUMMARY

According to one aspect, a system and method is providing for generating a display of a patient's internal anatomy for use in a surgical or interventional medical procedure based on a previously acquired high resolution baseline image and a newly acquired low resolution image. The high resolution image may be an image obtained during the procedure or a pre-procedure image such as a DRR. The low resolution image may be acquired using a pulse or low radiation dose. The system contemplates an image processing device configured to digitally manipulate the high resolution baseline image to produce a baseline image set including representative images of the baseline image at a plurality of permutations of movements of the baseline image in 4D or 6D space. The new low resolution image is compared to the baseline image set to select a representative image having an acceptable degree of correlation with the new image. The image processing device may implement algorithms to perform the comparison, such as a principal component analysis or other statistical test. The image processing device is further configured to merge the selected representative high resolution image with the new low resolution image to generate a merged image to be displayed. The merged image may be further processed to allow alternating between the selected high resolution image and the new low resolution image, or to adjust the amount that the two images are merged in the displayed image.

In another feature of the present disclosure, an imaging system may include an image processing device that acts as a viewfinder as the imaging device is moved relative to the patient. In accordance with this feature, an image of the surgical field is acquired with the imaging device in a first orientation. That acquired image is continuously displayed while the imaging device, patient or patient table is moved from the first orientation. This movement is tracked is used the image processing device to move the displayed image in relation to the tracked movement. With this feature, the display acts as a viewfinder to predict how a new image would appear if captured at that time by the imaging device. This feature can thus be used to determine where the next live image of the patient's anatomy will be taken or can be used to assist in stitching multiple images together to form a larger panoramic view o the surgical field. The image processing system may implement software adapted to optimize the predicted image and minimize misalignment or off angle appearance of the display. In another aspect, the image processing system permits annotation of the displayed image to identify anatomic features or desired image trajectories or alignments.

In a further feature of the disclosed embodiments, a baseline image of anatomy within a surgical field is acquired in a baseline orientation, and that baseline image is digitally manipulated to produce a baseline image set including representative images of the baseline image at a plurality of permutations of movements of the baseline image. A new image of the surgical field in which portions of the anatomy are blocked by objects. This new image is compared to the baseline image set to select a representative image having an acceptable degree of correlation with the new image. The image processing system generates a displayed image showing the surgical field with the blocking objects minimized or eliminated. The system further permits fading the blocked objects in and out of the display.

DESCRIPTION OF THE FIGURES

FIG. 2a is an image of a surgical field acquired using a full dose of radiation in the imaging system.

FIG. 2b is an image of the surgical field shown in FIG. 2a in which the image was acquired using a lower dose of radiation.

FIG. 2c is a merged image of the surgical field with the two images shown in FIGS. 2a-b merged in accordance with one aspect of the present disclosure.

FIG. 4a is an image of a surgical field including an object blocking a portion of the anatomy.

FIG. 4b is an image of the surgical field shown in FIG. 4a with the image of FIG. 4a partially merged with a baseline image to display the blocked anatomy.

FIGS. 6a-b are displays of the surgical field adjusted for movement of the imaging device or C-arm and providing an indicator of an in-bounds or out-of-bounds position of the imaging device for acquiring a new image.

FIGS. 7a-b are displays of the surgical field adjusted for movement of the imaging device or C-arm and providing an indicator of when a new image can be stitched to a previously acquired image.

FIGS. 8a-b are displays of the surgical field adjusted for movement of the imaging device or C-arm and providing an indicator of alignment of the imaging device with a desired trajectory for acquiring a new image.

DETAILED DESCRIPTION

Figure 1:
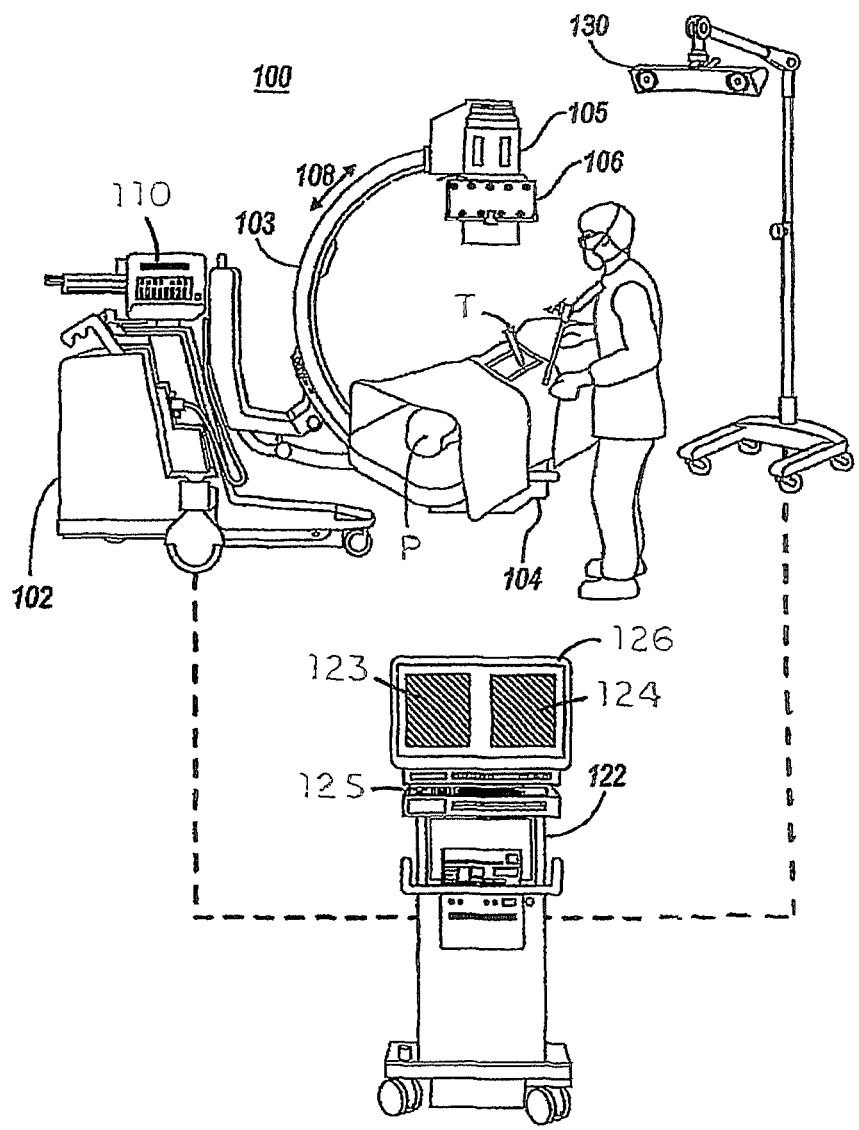
FIG. 1 is a pictorial view of an image guided surgical setting including an imaging system and an image processing device, as well as a tracking device.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

A typical imaging system 100 is shown in FIG. 1. The imaging system includes a base unit 102 supporting a C-arm imaging device 103. The C-arm includes a radiation source 104 that is positioned beneath the patient P and that directs a radiation beam upward to the receiver 105. It is known that the radiation beam emanated from the source 104 is conical so that the field of exposure may be varied by moving the source closer to or away from the patient. The C-arm 103 may be rotated about the patient P in the direction of the arrow 108 for different viewing angles of the surgical site. In some instances, implants or instruments T may be situated at the surgical site, necessitating a change in viewing angle for an unobstructed view of the site. Thus, the position of the receiver relative to the patient, and more particularly relative to the surgical site of interest, may change during a procedure as needed by the surgeon or radiologist. Consequently, the receiver 105 may include a tracking target 106 mounted thereto that allows tracking of the position of the C-arm using a tracking device 130. For instance, the tracking target 106 may include several infrared emitters spaced around the target, while the tracking device is configured to triangulate the position of the receiver 105 from the infrared signals emitted by the element. The base unit 102 includes a control panel 110 through which a radiology technician can control the location of the C-arm, as well as the radiation exposure. A typical control panel 110 thus permits the technician to "shoot a picture" of the surgical site at the surgeon's direction, control the radiation dose, and initiate a radiation pulse image.

The receiver 105 of the C-arm 103 transmits image data to an image processing device 122. The image processing device can include a digital memory associated therewith and a processor for executing digital and software instructions. The image processing device may also incorporate a frame grabber that uses frame grabber technology to create a digital image for projection as displays 123, 124 on a display device 126. The displays are positioned for interactive viewing by the surgeon during the procedure. The two displays may be used to show a images from two views, such as lateral and AP, or may show a baseline scan and a current scan of the surgical site, or a current scan and a "merged" scan based on a prior baseline scan and a low radiation current scan, as described herein. An input device 125, such as a keyboard or a touch screen, can allow the surgeon to select and manipulate the on-screen images. It is understood that the input device may incorporate an array of keys or touch screen icons corresponding to the various tasks and features implemented by the image processing device 122. The image processing device includes a processor that converts the image data obtained from the receiver 105 into a digital format.

In one aspect of the present invention, the image processing device 122 is configured to provide high quality real-time images on the displays 123, 124 that are derived from lower detail images obtained using lower doses of radiation. By way of example, FIG. 2a is a "full dose" (FD) x-ray image, while FIG. 2b is a low dose and/or pulsed (LD) image of the same anatomy. It is apparent that the LD image is too "noisy" and does not provide enough information about the local anatomy for accurate image guided surgery. While the FD image provides a crisp view of the surgical site, the higher radiation dose makes taking multiple FD images during a procedure highly problematic. Using the steps described herein, the surgeon is provided with a current image shown in FIG. 2c that significantly reduces the noise of the LD image, in some cases by about 90%, so that surgeon is provided with a clear real-time image using a low dose of radiation. This capability allows for dramatically less radiation exposure during the imaging to verify the position of instruments and implants during the procedure.

Figure 3:
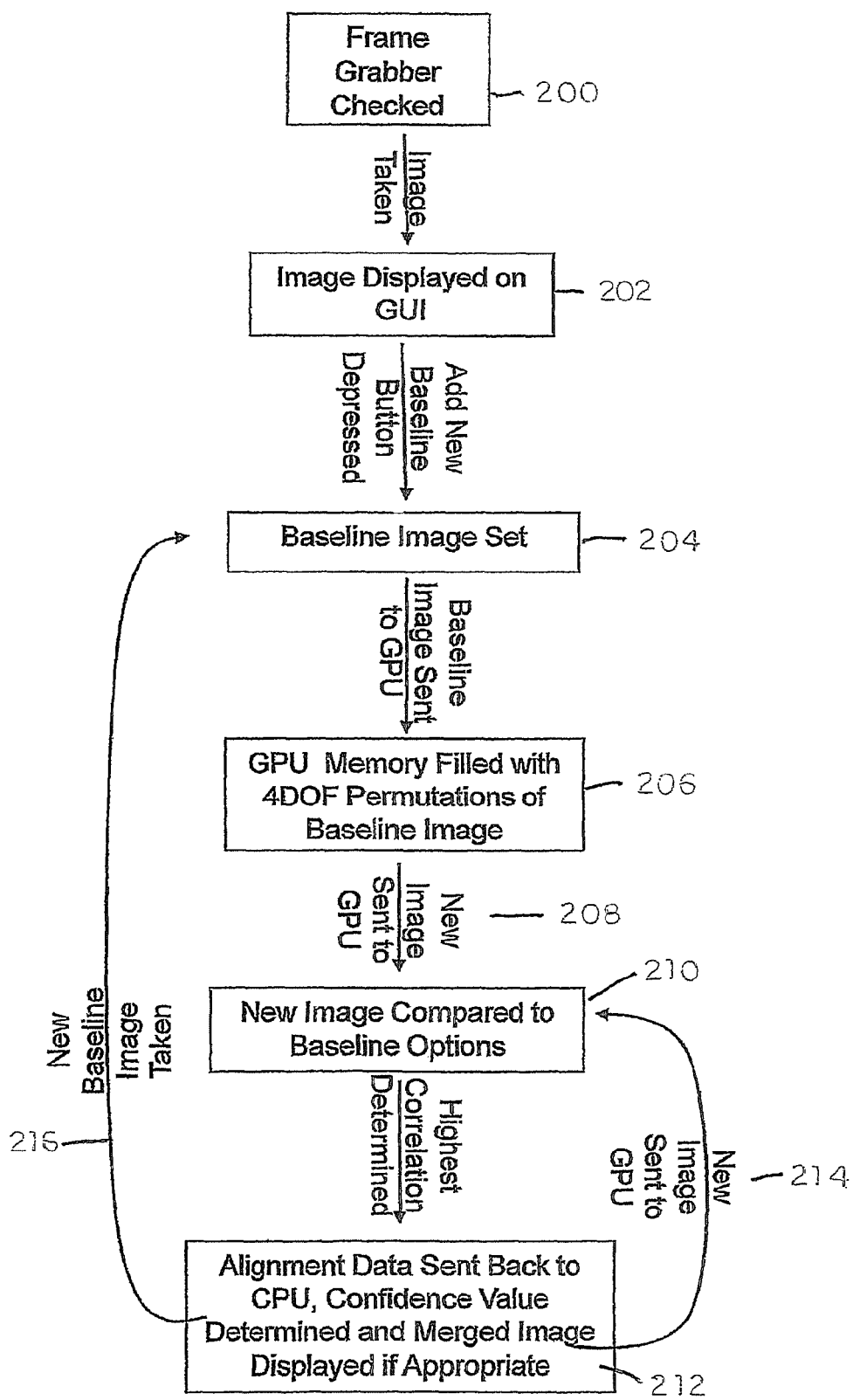
FIG. 3 is a flowchart of graphics processing steps undertaken by the image processing device shown in FIG. 1.

The flowchart of FIG. 3 depicts one embodiment of method according to the present invention. In a first step 200, a baseline high resolution FD image is acquired of the surgical site and stored in a memory associated with the image processing device. In some cases where the C-arm is moved during the procedure, multiple high resolution images can be obtained at different locations in the surgical site, and then these multiple images "stitched" together to form a composite base image (as discussed below). Movement of the C-arm, and more particularly "tracking" the acquired image during these movements, is accounted for in other steps described in more detail herein. For the present discussion it is assumed that the imaging system is relative fixed, meaning that only very limited movement of the C-arm and/or patient are contemplated, such as might arise in an epidural pain procedure, spinal K-wire placement or stone extraction. The baseline image is projected in step 202 on the display 123 for verification that the surgical site is properly centered within the image. In some cases, new FD images may be obtained until a suitable baseline image is obtained. In procedures in which the C-arm is moved, new baseline images are obtained at the new location of the imaging device, as discussed below. If the displayed image is acceptable as a baseline image, a button may be depressed on a user interface, such as on the display device 126 or interface 125.

Once the baseline image is acquired, a baseline image set is generated in step 204 in which the original baseline image is digitally rotated, translated and resized to create thousands of permutations of the original baseline image. For instance, a typical two dimensional (2D) image of 128×128 pixels may be translated ±15 pixels in the x and y directions at 1 pixel intervals, rotated ±9° at 3° intervals and scaled from 92.5% to 107.5% at 2.5% intervals (4 degrees of freedom, 4D), yielding 47,089 images in the baseline image set. (A three-dimensional (3D) image will imply a 6D solution space due to the addition of two additional rotations orthogonal to the x and y axis. An original CT image data set can be used to form many thousands of DRRs in a similar fashion.) Thus, in this step, the original baseline image spawns thousands of new image representations as if the original baseline image was acquired at each of the different movement permutations. This "solution space" may be stored in a graphics card memory of the image processing device 122 in step 206 or formed as a new image is sent to the GPU, depending on the number of images in the solution space and the speed at which the GPU can produce those images. With current computing power, on a free standing, medical grade computer, the generation of this baseline image set can occur in less than one second.

During the procedure, a new LD image is acquired in step 208, stored in the memory associated with the image processing device, and projected on display 123. Since the new image is obtained at a lower dose of radiation it is very noisy. The present invention thus provides steps for "merging" the new image with an image from the baseline image set to produce a clearer image on the second display 124 that conveys more useful information to the surgeon. The invention thus contemplates an image recognition or registration step 210 in which the new image is compared to the images in the baseline image set to find a statistically meaningful match. A new "merged" image is generated in step 212 that may be displayed on display 124 adjacent the view of the original new image. At various times throughout the procedure, a new baseline image may be obtained in step 216 that is used to generate a new baseline image set in step 204.

Step 210 contemplates comparing the current new image to the images in the baseline image set. Since this step occurs during the surgical procedure, time and accuracy are critical. Preferably, the step can obtain an image registration in less than one second so that there is no meaningful delay between when the image is taken by the C-arm and when the merged image is displayed on the device 126. Various algorithms may be employed that may be dependent on various factors, such as the number of images in the baseline image set, the size and speed of the computer processor or graphics processor performing the algorithm calculations, the time allotted to perform the computations, and the size of the images being compared (e.g., 128×128 pixels, 1024×1024 pixels, etc). In one approach, comparisons are made between pixels at predetermined locations described above in a grid pattern throughout 4D space. In another heuristic approach, pixel comparisons can be concentrated in regions of the images believed to provide a greater likelihood of a relevant match. These regions may be "pre-seeded" based on knowledge from a grid or PCA search (defined below) or data from a tracking system (such as an optical surgical navigation device) or location data from the DICOM file or the equivalent.

In another approach, a principal component analysis (PCA) is performed, which can allow for comparison to a larger number of larger images in the allotted amount of time than is permitted with the full resolution grid approach. In the PCA approach, a determination is made as to how each pixel of the image set co-varies with each other. A covariance matrix may be generated using only a small portion of the total solution set—for instance, a randomly selected 10% of the baseline image set. Each image from the baseline image set is converted to a column vector. In one example, a 70×40 pixel image becomes a 2800×1 vector. These column vectors are normalized to a mean of 0 and a variance of 1 and combined into a larger matrix. The covariance matrix is determined from this larger matrix and the largest eigenvectors are selected. For this particular example, it has been found that 30 PCA vectors can explain about 80% of the variance of the respective images. Thus, each 2800×1 image vector can be multiplied by a 2800×30 PCA vector to yield a 1×30 vector. The same steps are applied to the new image—the new image is converted to a 2800×1 image vector and multiplication with the 2800×30 PCA vector produces a 1/30 vector corresponding to the new image. The solution set (baseline image) vectors and the new image vector are normalized and the dot product of the new image vector to each vector in the solution space is calculated. The solution space baseline image vector that yields the largest dot product (i.e., closest to 1) is determined to be the closest image to the new image. It is understood that the present example may be altered with different image sizes and/or different principal components used for the analysis. It is further understood that other known techniques may be implemented that may utilize eigenvectors, singular value determination, mean squared error, mean absolute error, and edge detection, for instance. It is further contemplated that various image recognition approaches can be applied to selected regions of the images or that various statistical measures may be applied to find matches falling within a suitable confidence threshold. A confidence or correlation value may be assigned that quantifies the degree of correlation between the new image and the selected baseline image, or selected ones of the baseline image set, and this confidence value may be displayed for the surgeon's review. The surgeon can decide whether the confidence value is acceptable for the particular display and whether another image should be acquired.

In the image guided surgical procedures, tools, implants and instruments will inevitably appear in the image field.

These objects are typically radiodense and consequently block the relevant patient anatomy from view. The new image obtained in step 210 will thus include an artifact of the tool T that will not correlate to any of the baseline image set. The presence of the tool in the image thus ensures that the comparison techniques described above will not produce a high degree of registration between the new image and any of the baseline image set. Nevertheless, if the end result of each of the above procedures is to seek out the highest degree of correlation, which is statistically relevant or which exceeds a certain threshold, the image registration may be conducted with the entire new image, tool artifact and all.

Alternatively, the image registration steps may be modified to account for the tool artifacts on the new image. In one approach, the new image may be evaluated to determine the number of image pixels that are "blocked" by the tool. This evaluation can involve comparing a grayscale value for each pixel to a threshold and excluding pixels that fall outside that threshold. For instance, if the pixel grayscale values vary from 0 (completely blocked) to 10 (completely transparent), a threshold of 3 may be applied to eliminate certain pixels from evaluation. Additionally, when location data is available for various tracked tools, algorithmically areas that are blocked can be mathematically avoided.

Figure 5A:
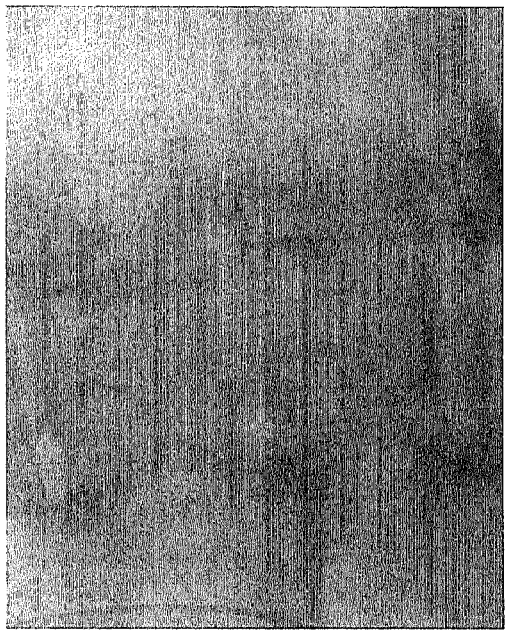
FIGS. 5a-b are baseline and merged images of a surgical field including a blocking object.
Figure 5B:
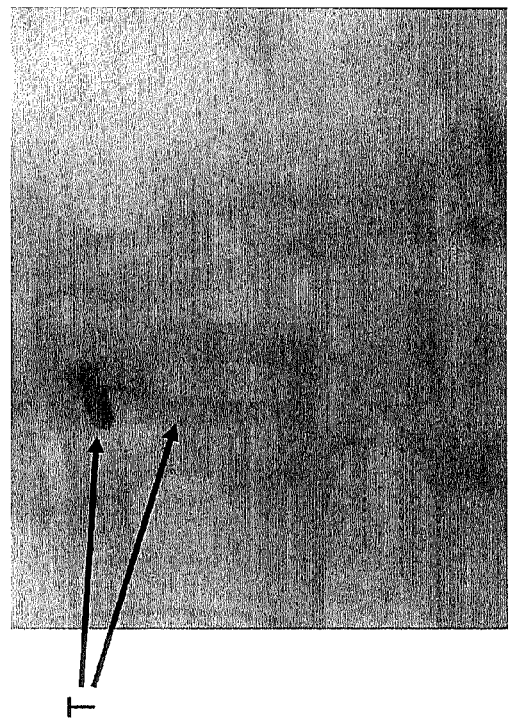

Once the image registration is complete, the new image may be displayed with the selected image from the baseline image set in different ways. In one approach, the two images are merged, as illustrated in FIGS. 4a, b. The original new image is shown in FIG. 4a with the instrument T plainly visible and blocking the underlying anatomy. A partially merged image generated in step 212 (FIG. 3) is shown in FIG. 4b in which the instrument T is still visible but substantially mitigated and the underlying anatomy is visible. The two images may be merged by combining the digital representation of the images in a conventional manner, such as by adding or averaging pixel data for the two images. In one embodiment, the surgeon may identify a specific region of interest in the displayed image, such as through the user interface 125, and the merging operation can be configured to utilize the baseline image data for the display outside the region of interest and conduct the merging operation for the display within the region of interest. The user interface 125 may be provided with a "slider" that controls the amount the baseline image versus the new image that is displayed in the merged image. In another approach, the surgeon may alternate between the correlated baseline image and the new image or merged image, as shown in FIGS. 5a, b. The image in FIG. 5a is the image from the baseline image set found to have the highest degree of correlation to the new image. The image in FIG. 5b is the new image obtained. The surgeon may alternate between these views to get a clearer view of the underlying anatomy and a view of the current field with the instrumentation T, which in effect by alternating images digitally removes the instrument from the field of view, clarifying its location relative to the anatomy blocked by it.

As indicated above, the present invention also contemplates a surgical navigation procedure in which the imaging device or C-arm 103 is moved. Thus, the present invention contemplates tracking the position of the C-arm rather than tracking the position of the surgical instruments and implants as in traditional surgical navigation techniques, using commercially available tracking devices or the DICOM information from the imaging device. Tracking the C-arm requires a degree of accuracy that is much less than the accuracy required to track the instruments and implants. In this embodiment, the image processing device 122 receives tracking information from the tracking device 130. The object of this aspect of the invention is to ensure that the surgeon sees an image that is consistent with the actual surgical site regardless of the orientation of the C-arm relative to the patient.

Tracking the position of the C-arm can account for "drift", which is a gradual misalignment of the physical space and the imaging (or virtual) space. This "drift" can occur because of subtle patient movements, inadvertent contact with the table or imaging device and even gravity. This misalignment is often visually imperceptible, but can generate noticeable shifts in the image viewed by the surgeon. These shifts can be problematic when the surgical navigation procedure is being performed (and a physician is relying on the information obtained from this device) or when alignment of new to baseline images is required to improve image clarity. The use of image processing eliminates the inevitable misalignment of baseline and new images. The image processing device 122 further may incorporate a calibration mode in which the current image of the anatomy is compared to the predicted image. The difference between the predicted and actual movement of the image can be accounted for by an inaccurate knowledge of the "center of mass" or COM, described below, and drift. Once a few images are obtained and the COM is accurately established, recalibration of the system can occur automatically with each successive image taken and thereby eliminating the impact of drift.

The image processing device 122 may operate in a "tracking mode" in which the movement of the C-arm is monitored and the currently displayed image is moved accordingly. The currently displayed image may be the most recent baseline image, a new LD image or a merged image generated as described above. This image remains on one of the displays 123, 124 until a new picture is taken by the imaging device 100. This image is shifted on the display to match the movement of the C-arm using the position data acquired by the tracking device 130. A tracking circle 240 may be shown on the display, as depicted in FIGS. 6a, 6b. The tracking circle identifies an "in bounds" location for the image. When the tracking circle appears in red, the image that would be obtained with the current C-arm position would be "out of bounds" in relation to a baseline image position, as shown in FIG. 6a. As the C-arm is moved by the radiology technician the representative image on the display is moved. When the image moves "in bounds", as shown in FIG. 6b, the tracking circle 240 turns green so that the technician has an immediate indication that the C-arm is now in a proper position for obtaining a new image. The tracking circle may be used by the technician to guide the movements of the C-arm during the surgical procedure. The tracking circle may also be used to assist the technician in preparing a baseline stitched image. Thus, an image position that is not properly aligned for stitching to another image, as depicted in FIG. 7a, will have a red tracking circle 240, while a properly aligned image position, as shown in FIG. 7b, will have a green tracking circle. The technician can then acquire the image to form part of the baseline stitched image.

The present invention contemplates a feature that enhances the communication between the surgeon and the radiology technician. During the course of a procedure the surgeon may request images at particular locations or orientations. One example is what is known as a "Ferguson view" in spinal procedures in which an AP oriented C-arm is canted to align directly over a vertebral end plate with the end plate oriented "flat" or essentially parallel with the beam axis of the C-arm. Obtaining a Ferguson view requires rotating the C-arm or the patient table while obtaining multiple AP views of the spine, which is cumbersome and inaccurate using current techniques, requiring a number of fluoroscopic images to be performed to find the one best aligned to the endplate. The present invention allows the surgeon to overlay a grid onto a single image or stitched image and provide labels for anatomic features that can then be used by the technician to orient the C-arm. Thus, as shown in FIG. 8a, the image processing device 122 is configured to allow the surgeon to place a grid 245 within the tracking circle 240 overlaid onto a Lateral image. The surgeon may also locate labels 250 identifying anatomic structure, in this case spinal vertebrae. In this particular example, the goal is to align the L2-L3 disc space with the center grid line 246. To assist the technician, a trajectory arrow 255 is overlaid onto the image to indicate the trajectory of an image acquired with the C-arm in the current position. As the C-arm moves, changing orientation off of pure AP, the image processing device evaluates the C-arm position data obtained from the tracking device 230 to determine the new orientation for trajectory arrow 255. The trajectory arrow thus moves with the C-arm so that when it is aligned with the center grid line 246, as shown in FIG. 8b, the technician can shoot the image knowing that the C-arm is properly aligned to obtain a Ferguson view along the L3 endplate. Thus, monitoring the lateral view until it is rotated and centered along the center grid line allows the radiology technician to find the AP Ferguson angle without guessing and taking a number of incorrect images.

Figure 9:
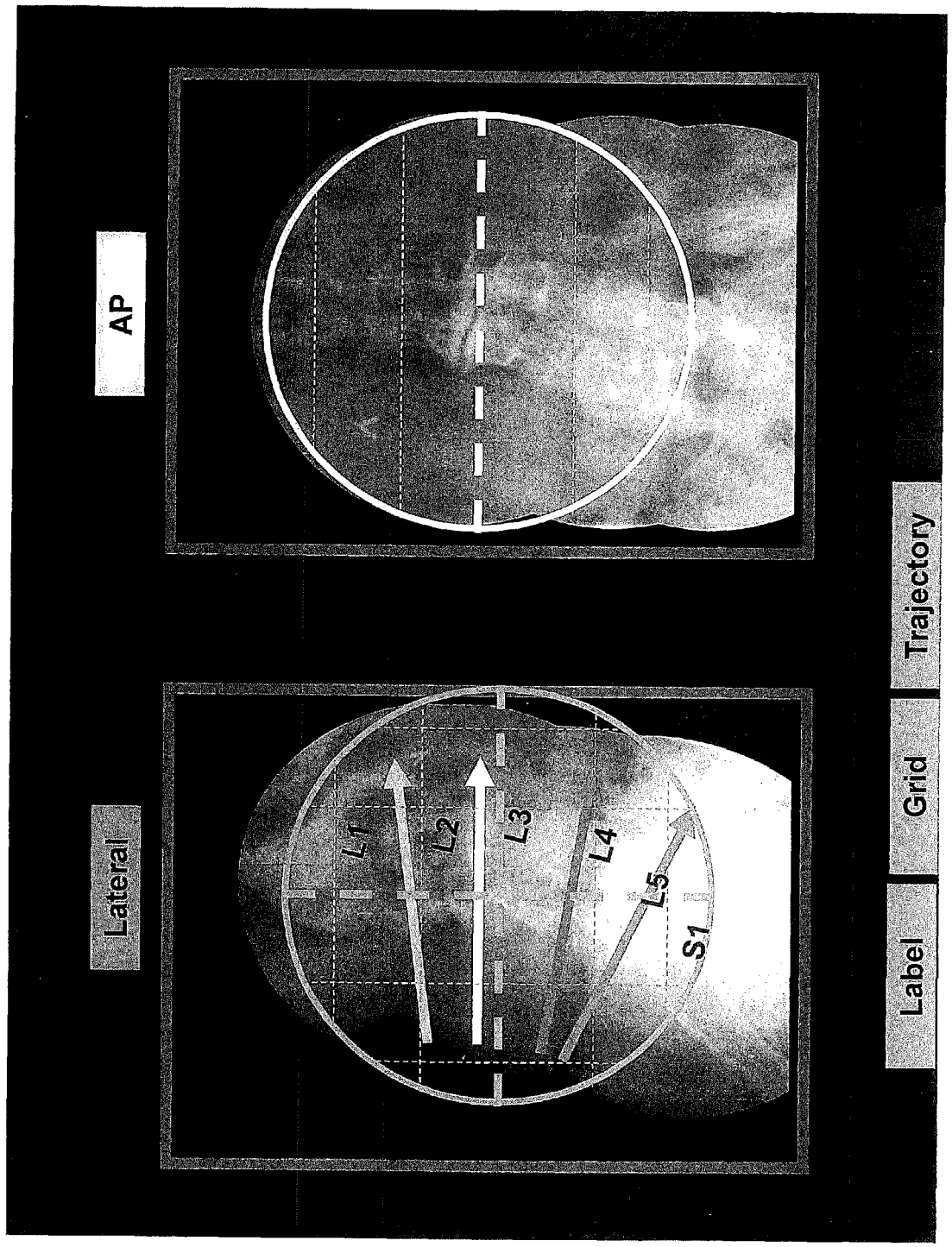
FIG. 9 is a depiction of a display and user interface for the image processing device shown in FIG. 1.

The image processing device may be further configured to show the lateral and AP views simultaneously on respective displays 123 and 124, as depicted in FIG. 9. Either or both views may incorporate the grid, labels and trajectory arrows. This same lateral view may appear on the control panel 110 for the imaging system 100 for viewing by the technician. As the C-arm is moved to align the trajectory arrow with the center grid line, as described above, both the lateral and AP images are moved accordingly so that the surgeon has an immediate perception of what the new image will look like. Again, once the technician properly orients the C-arm, as indicated by alignment of the trajectory arrow with the center grid line, a new AP image is acquired. As shown in FIG. 9, a view may include multiple trajectory arrows, each aligned with a particular disc space. For instance, the uppermost trajectory arrow is aligned with the L1-L2 disc space, while the lowermost arrow is aligned with the L5-S1 disc space. In multiple level procedures the surgeon may require a Ferguson view of different levels, which can be easily obtained by requesting the technician to align the C-arm with a particular trajectory arrow.

Figure 10:
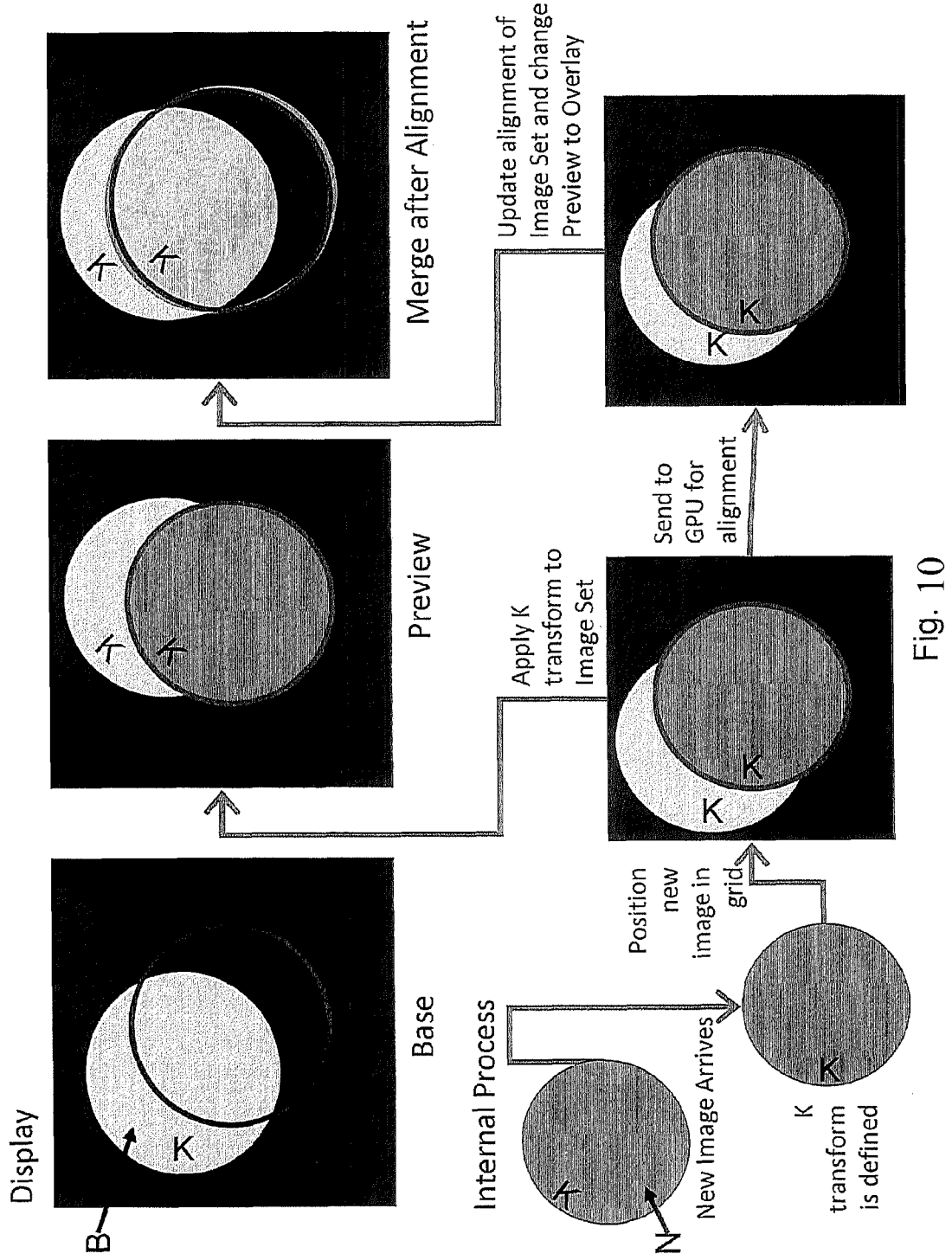
FIG. 10 is a graphical representation of an image alignment process according to the present disclosure.

In another feature, a radiodense asymmetric shape can be placed in a known location on the C-arm detector. This creates the ability to link the coordinate frame of the C-arm to the arbitrary orientation of the C-arm's image coordinate frame. As the C-arm's display may be modified to generate an image having any rotation or mirroring, detecting this shape radically simplifies the process of image comparison and image stitching. Thus, as shown in FIG. 10, the baseline image B includes the indicia "K" at the 9 o'clock position of the image. The new image N is obtained in which the indicia has been rotated by the physician or technologist away from the default orientation. Comparing this new image to the baseline image set is unlikely to produce any registration between images due to this angular offset. In one embodiment, the image processing device detects the actual rotation of the C-arm from the baseline orientation while in another embodiment the image processing device uses image recognition software to locate the "K" indicia in the new image and determine the angular offset from the default position. This angular offset is used to alter the rotation and/or mirror image the baseline image set. The baseline image selected in the image registration step 210 is maintained in its transformed orientation to be merged with the newly acquired image. This transformation can include rotation and mirror-imaging, to eliminate the display effect that is present on a C-arm.

In another aspect, it is known that as the C-arm radiation source 104 moves closer to the table, the size of the image captured by the receiver 105 becomes larger; moving the receiver closer to the table results in a decrease in image size. Whereas the amount that the image scales with movements towards and away from the body can be easily determined, if the C-arm is translated along the table, the image will shift, with the magnitude of that change depending upon the proximity of the "center of mass" (COM) of the patient to the radiation source. Although the imaged anatomy is of 3D structures, with a high degree of accuracy, mathematically we can represent this anatomy as a 2D picture of the 3D anatomy placed at the COM of the structures. Then, for instance, when the COM is close to the radiation source, small movements will cause the resulting image to shift greatly. Until the COM is determined, though, the calculated amount that the objects on the screen shift will be proportional to but not equal to their actual movement. The difference is used to calculate the actual location of the COM. The COM is adjusted based on the amount that those differ, moving it away from the radiation source when the image shifted too much, and the opposite if the image shifts too little. The COM is initially assumed to be centered on the table to which the reference arc of the tracking device is attached. The true location of the COM is fairly accurately determined using the initial two or three images taken during initial set-up of the imaging system, and reconfirmed/adjusted with each new image taken. Once the COM is determined in global space, the movement of the C-arm relative to the COM can be calculated and applied to translate the baseline image set accordingly for image registration.

The image processing device 122 may also be configured to allow the surgeon to introduce other tracked elements into an image, to help guide the surgeon during the procedure. A closed-loop feedback approach allows the surgeon to confirm that the location of this perceived tracked element and the image taken of that element correspond. Specifically, the live x-ray and the determined position from the surgical navigation system are compared. In the same fashion that knowledge of the baseline image, through image recognition, can be used to track the patient's anatomy even if blocked by radiodense objects, knowledge of the radiodense objects, when the image taken is compared to their tracked location, can be used to confirm their tracking. When both the instrument/implant and the C-arm are tracked, the location of the anatomy relative to the imaging source and the location of the equipment relative to the imaging source are known. This information can thus be used to quickly and interactively ascertain the location of the equipment or hardware relative to the anatomy. This feature can, by way of example, have particular applicability to following the path of a catheter in an angio procedure, for instance. In a typical angio procedure, a cine, or continuous fluoro, is used to follow the travel of the catheter along a vessel. The present invention allows intersplicing previously generated images of the anatomy with the virtual depiction of the catheter with live fluoro shots of the anatomy and actual catheter. Thus, rather than taking 15 fluoro shots per second for a typical cine procedure, the present invention allows the radiology technician to take only one shot per second to effectively and accurately track the catheter as it travels along the vessel. The previously generated images are spliced in to account for the fluoro shots that are not taken. The virtual representations can be verified to the live shot when taken and recalibrated if necessary.

In certain procedures it is possible to fix the position of the vascular anatomy to larger features, such as nearby bones. This can be accomplished using DRRs from prior CT angiograms (CTA) or from actual angiograms taken in the course of the procedure. Either, approach may be used as a means to link angiograms back to bony anatomy and vice versa. To describe in greater detail, the same CTA may be used to produce different DRRs, such as DRRs highlighting just the bony anatomy and another in a matched set that includes the vascular anatomy along with the bones. A baseline fluoro image taken of the patient's bony anatomy can then be compared with the bone DRRs to determine the best match. Instead of displaying the result using bone only DRR, the matched DRR that includes the vascular anatomy can be used to merge with the new image. In this approach, the bones help to place the radiographic position of the catheter to its location within the vascular anatomy. Since it is not necessary to continually image the vessel itself, as the picture of this structure can be overlaid onto the bone only image obtained, the use of contrast dye can be limited versus prior procedures in which the contrast dye is necessary to constantly see the vessels.

Following are examples of specific procedures utilizing the features of the image processing device discussed above. These are just a few examples as to how the software can be manipulated using different combinations of baseline image types, display options, and radiation dosing and not meant to be an exhaustive list.

Pulsed New Image/Alternated with/Baseline of FD Fluoro or Preoperative X-Ray

A pulsed image is taken and compared with a previously obtained baseline image set containing higher resolution non-pulsed image(s) taken prior to the surgical procedure. Registration between the current image and one of the baseline solution set provides a baseline image reflecting the current position and view of the anatomy. The new image is alternately displayed or overlaid with the registered baseline image, showing the current information overlaid and alternating with the less obscured or clearer image.

Pulsed New Image/Alternated with/Baseline Derived from DRR

A pulsed image is taken and compared with a previously obtained solution set of baseline images, containing higher resolution DRR obtained from a CT scan. The DRR image can be limited to just show the bony anatomy, as opposed to the other obscuring information that frequently "cloud" a film taken in the OR (e.g.—bovie cords, EKG leads, etc.) as well as objects that obscure bony clarity (e.g.—bowel gas, organs, etc.). As with the above example, the new image that is registered with one of the prior DRR images, and these images are alternated or overlaid on the display 123, 124.

Pulsed New Image/Merged Instead of Alternated

All of the techniques described above can be applied and instead of alternating the new and registered baseline images, the prior and current image are merged. By performing a weighted average or similar merging technique, a single image can be obtained which shows both the current information (e.g.—placement of instruments, implants, catheters, etc.) in reference to the anatomy, merged with a higher resolution picture of the anatomy. In one example, multiple views of the merger of the two images can be provided, ranging from 100% pulsed image to 100% DRR image. A slide button on the user interface 125 allows the surgeon to adjust this merger range as desired.

New Image is a Small Segment of a Larger Baseline Image Set

The imaging taken at any given time contains limited information, a part of the whole body part. Collimation, for example, lowers the overall tissue radiation exposure and lowers the radiation scatter towards physicians but at the cost of limiting the field of view of the image obtained. Showing the actual last projected image within the context of a larger image (e.g.—obtained prior, preoperatively or intraoperatively, or derived from CTs)—merged or alternated in the correction location—can supplement the information about the smaller image area to allow for incorporation into reference to the larger body structure(s). The same image registration techniques are applied as described above, except that the registration is applied to a smaller field within the baseline images (stitched or not) corresponding to the area of view in the new image.

Same as Above, Located at Junctional or Blocked Areas

Not infrequently, especially in areas that have different overall densities (e.g.—chest vs. adjacent abdomen, head/neck/cervical spine vs. upper thorax), the area of an x-ray that can be clearly visualized is only part of the actual image obtained. This can be frustrating to the physician when it limits the ability to place the narrow view into the larger context of the body or when the area that needs to be evaluated is in the obscured part of the image. By stitching together multiple images, each taken in a localized ideal environment, a larger image can be obtained. Further, the current image can be added into the larger context (as described above) to fill in the part of the image clouded by its relative location.

Unblocking the Hidden Anatomy or Mitigating its Local Effects

As described above, the image processing device performs the image registration steps between the current new image and a baseline image set that, in effect, limits the misinformation imparted by noise, be it in the form of x-ray scatter or small blocking objects (e.g.—cords, etc.) or even larger objects (e.g.—tools, instrumentation, etc.). In many cases, it is that part of the anatomic image that is being blocked by a tool or instrument that is of upmost importance to the surgery being performed. By eliminating the blocking objects from the image the surgery becomes safer and more efficacious and the physician becomes empowered to continue with improved knowledge. Using an image that is taken prior to the noise being added (e.g.—old films, baseline single FD images, stitched together fluoro shots taken prior to surgery, etc.) or idealized (e.g.—DRRs generated from CT data), displaying that prior "clean" image, either merged or alternated with the current image, will make those objects disappear from the image or become shadows rather than dense objects. If these are tracked objects, then the blocked area can be further deemphasized or the information from it can be eliminated as the mathematical comparison is being performed, further improving the speed and accuracy of the comparison.

The image processing device configured as described herein provides three general features that (1) reduce the amount of radiation exposure required for acceptable live images, (2) provide images to the surgeon that can facilitate the surgical procedure, and (3) improve the communication between the radiology technician and the surgeon. With respect to the aspect of reducing the radiation exposure, the present invention permits low dose images to be taken throughout the surgical procedure and fills in the gaps created by "noise" in the current image to produce a composite or merged image of the current field of view with the detail of a full dose image. In practice this allows for highly usable, high quality images of the patient's anatomy generated with an order of magnitude reduction in radiation exposure than standard FD imaging using unmodified features present on all common, commercially available C-arms. The techniques for image registration described herein can be implemented in a graphic processing unit and can occur in a second or so to be truly interactive; when required such as in CINE mode, image registration can occur multiple times per second. A user interface allows the surgeon to determine the level of confidence required for acquiring registered image and gives the surgeon options on the nature of the display, ranging from side-by-side views to fade in/out merged views.

With respect to the feature of providing images to the surgeon that facilitate the surgical procedure, several digital imaging techniques can be used to improve the user's experience. One example is an image tracking feature that can be used to maintain the image displayed to the surgeon in an essentially a "stationary" position regardless of any position changes that may occur between image captures. In accordance with this feature, the baseline image can be fixed in space and new images adjust to it rather than the converse. When successive images are taken during a step in a procedure each new image can be stabilized relative to the prior images so that the particular object of interest (e.g.—anatomy or instrument) is kept stationary in successive views. For example, as sequential images are taken as a bone screw is introduced into a body part, the body part remains stationary on the display screen so that the actual progress of the screw can be directly observed.

In another aspect of this feature, the current image including blocking objects can be compared to earlier images without any blocking objects. In the registration process, the image processing device can generate a merged image between new image and baseline image that deemphasizes the blocking nature of the object from the displayed image. The user interface also provides the physician with the capability to fade the blocking object in and out of the displayed view.

In other embodiments in which the object itself is being tracked, a virtual version of the blocking object can be added back to the displayed image. The image processing device can obtain position data from a tracking device following the position of the blocking object and use that position data to determine the proper location and orientation of the virtual object in the displayed image. The virtual object may be applied to a baseline image to be compared with a new current image to serve as a check step—if the new image matches the generated image (both tool and anatomy) within a given tolerance then the surgery can proceed. If the match is poor, the surgery can be stopped (in the case of automated surgery) and/or recalibration can take place. This allows for a closed-loop feedback feature to facilitate the safety of automation of medical intervention.

For certain procedures, such as a pseudo-angio procedure, projecting the vessels from a baseline image onto current image can allow a physician to watch a tool (e.g.—microcatheter, stent, etc.) as it travels through the vasculature while using much less contrast medium load. The adjacent bony anatomy serves as the "anchor" for the vessels—the bone is essentially tracked, through the image registration process, and the vessel is assumed to stay adjacent to this structure. In other words, when the anatomy moves between successive images, the new image is registered to a different one of the baseline image set that corresponds to the new position of the "background" anatomy. The vessels from a different but already linked baseline image containing the vascular structures can then be overlaid or merged with the displayed image which lacks contrast. If necessary or desired, intermittent angios can be taken to confirm. When combined with a tracked catheter, a working knowledge of the location of the instrument can be included into the images. A cine (continuous movie loop of fluoro shots commonly used when an angiogram is obtained) can be created in which generated images are interspliced into the cine images, allowing for many fewer x-rays to be obtained while an angiogram is being performed or a catheter is being placed. Ultimately, once images have been linked to the original baseline image, any of these may be used to merge into a current image, producing a means to monitor movement of implants, the formation of constructs, the placement of stents, etc.

In the third feature—improving communication—the image processing device described herein allows the surgeon to annotate an image in a manner that can help guide the technician in the positioning of the C-arm as to how and where to take a new picture. Thus, the user interface 125 of the image processing device 122 provides a vehicle for the surgeon to add a grid to the displayed image, label anatomic structures and identify trajectories for alignment of the imaging device. As the technician moves the imaging device or C-arm, the displayed image is moved. This feature allows the radiology tech to center the anatomy that is desired to be imaged in the center of the screen, at the desired orientation, without taking multiple images each time the C-arm is brought back in the field to obtain this. This feature provides a view finder for the C-arm, a feature lacking currently. The technician can activate the C-arm to take a new image with a view tailored to meet the surgeon's expressed need.

In addition, linking the movements of the C-arm to the images taken using DICOM data or a surgical navigation backbone, for example, helps to move the displayed image as the C-arm is moved in preparation for a subsequent image acquisition. "In bound" and "out of bounds" indicators can provide an immediate indication to the technician whether a current movement of the C-arm would result in an image that cannot be correlated or registered with any baseline image, or that cannot be stitched together with other images to form a composite field of view. The image processing device thus provides image displays that allow the surgeon and technician to visualize the effect of a proposed change in location and trajectory of the c-arm. Moreover, the image processing device may help the physician, for instance, alter the position of the table or the angle of the C-arm so that the anatomy is aligned properly (such as parallel or perpendicular to the surgical table). The image processing device can also determine the center of mass (COM) of the exact center of an x-rayed object using two or more x-ray shots from two or more different gantry angles/positions, and then use this COM information to improve the linking of the physical space (in millimeters) to the displayed imaging space (in pixels).

The image recognition component disclosed herein can overcome the lack of knowledge of the location of the next image to be taken, which provides a number of benefits. Knowing roughly where the new image is centered relative to the baseline can limit the need to scan a larger area of the imaging space and, therefore, significantly increase the speed of image recognition software. Greater amounts of radiation reduction (and therefore noise) can be tolerated, as there exists an internal check on the image recognition. Multiple features that are manual in the system designed without surgical navigation, such as baseline image creation, switching between multiple baseline image sets, and stitching, can be automated. These features are equally useful in an image tracking context.

As described above, the systems and methods correlate or synchronize the previously obtained images with the live images to ensure that an accurate view of the surgical site, anatomy and hardware, is presented to the surgeon. In an optimum case, the previously obtained images are from the particular patient and are obtained near in time to the surgical procedure. However, in some cases no such prior image is available. In such cases, the "previously obtained image" can be extracted from a database of CT and DRR images. The anatomy of most patients is relatively uniform depending on the height and stature of the patient. From a large database of images there is a high likelihood that a prior image or images of a patient having substantially similar anatomy can be obtained. The image or images can be correlated to the current imaging device location and view, via software implemented by the image processing device 122, to determine if the prior image is sufficiently close to the anatomy of the present patient to reliably serve as the "previously obtained image" to be interspliced with the live images.

The display in FIG. 9 is indicative of the type of display and user interface that may be incorporated into the image processing device 122, user interface 125 and display device 126. For instance, the display device may include the two displays 122, 123 with "radio" buttons or icons around the perimeter of the display. The icons may be touch screen buttons to activate the particular feature, such as the "label", "grid" and "trajectory" features shown in the display. Activating a touch screen or radio button can access a different screen or pull down menu that can be used by the surgeon to conduct the particular activity. For instance, activating the "label" button may access a pull down menu with the labels "L1", "L2", etc., and a drag and drop feature that allows the surgeon to place the labels at a desire location on the image. The same process may be used for placing the grid and trajectory arrows shown in FIG. 9.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method for generating a display of an image of a patient's internal anatomy in a surgical field during a medical procedure, comprising:
   acquiring a high resolution baseline image of the surgical field including the patient's internal anatomy in a baseline orientation;
   digitally manipulating the high resolution baseline image to produce a baseline image set including representative images of the baseline image at a plurality of permutations of movements of the baseline image from the baseline orientation;
   acquiring a new image of the surgical field at a lower resolution;
   comparing the new image to the representative images in the baseline image set and selecting the representative image having an acceptable degree of correlation with the new image; and
   merging the selected representative image with the new image and displaying the merged image.

2. The method of claim 1, wherein the baseline image is selected from the group including a pre-procedure full dose fluoroscopic image, a DRR and a CT scan image.

3. The method of claim 1, wherein the new image is one of a pulse or low dose image.

4. The method of claim 1, wherein:
   in the step of digitally manipulating the high resolution image the permutations of movements form a predefined grid of image movements; and
   the step of comparing the new image to the representative images of the baseline image set includes comparing overlapping pixels between the representative image and the new image.

5. The method of claim 1, wherein the step of comparing the new image to the representative images of the baseline image set includes:
   performing a principal component analysis (PCA) on the pixels of the representative images in the baseline image set to generate one or more PCA vectors;
   producing a PCA matrix of PCA vectors for each pixel in a representative image;
   generating a column vector for each representative image and the new image of pixel data for each pixel in the image;
   performing a matrix multiplication of the PCA matrix and each column vector to generate a new column vector for each representative image and the new image;
   obtaining the dot product of the column vector for the new image and the column vector for each of the representative image; and
   selecting a representative image for which the dot product is within a pre-determined threshold.

6. The method of claim 1, in which the medical procedure includes tools, instruments, implants or other objects that block or obscure the internal anatomy in an image of the surgical field, wherein the step of comparing the new image to the representative images of the baseline image set includes only comparing portions of the images outside the portions that are blocked or obscured.

7. The method of claim 6, wherein the location of the blocked or obscured portions of the new image are determined by determining which pixels have a value outside a pre-determined threshold.

8. The method of claim 1, wherein:
   the step of digitally manipulating the high resolution baseline image includes providing parallel images to each representative image in which the image of certain anatomic features is reduced or enhanced; and
   the step of merging the selected representative image includes merging and displaying the parallel image to the selected representative image.

9. An image processing device for generating a display of an image of a patient's internal anatomy during a medical procedure, comprising:
   a memory for storing a high resolution baseline image of the surgical field including the patient's internal anatomy in a baseline orientation and a new image of the surgical field at a low resolution; and
   a processor configured to;
      digitally manipulate the high resolution baseline image to produce a baseline image set including representative images of the baseline image at a plurality of permutations of movements of the baseline image from the baseline orientation;
      perform software instructions for comparing the new image to the representative images in the baseline image set and selecting the representative image having an acceptable degree of correlation with the new image;
      digitally merge the selected representative image with the new image; and generate signals for displaying the merged image on a display device.

10. The image processing device of claim 9, wherein:
the processor is further configured to digitally manipulate the high resolution image such that the permutations of movements form a predefined grid of image movements; and
the software instructions for comparing the new image to the representative images of the baseline image set include instructions for comparing overlapping pixels between the representative image and the new image.

11. The image processing device of claim 9, wherein the software instructions for comparing the new image to the representative images of the baseline image set include instructions for:
performing a principal component analysis (PCA) on the pixels of the representative images in the baseline image set to generate one or more PCA vectors;
producing a PCA matrix of PCA vectors for each pixel in a representative image;
generating a column vector for each representative image and the new image of pixel data for each pixel in the image;
performing a matrix multiplication of the PCA matrix and each column vector to generate a new column vector for each representative image and the new image;
obtaining the dot product of the column vector for the new image and the column vector for each of the representative image; and
selecting a representative image for which the dot product is within a pre-determined threshold.

12. The image processing device of claim 9, in which the medical procedure includes tools, instruments, implants or other objects that block or obscure the internal anatomy in an image of the surgical field, wherein the software instructions for comparing the new image to the representative images of the baseline image set include instructions for only comparing portions of the images outside the portions that are blocked or obscured.

13. The image processing device of claim 12, wherein the processor is configured to determine the location of the blocked or obscured portions of the new image by determining which pixels of the representative images have a value outside a pre-determined threshold.

14. The image processing device of claim 9, further comprising a user interface operable to allow manual adjustment of the degree of digitally merging the selected representative image with the new image.

15. The image processing device of claim 14, wherein:
the user interface is further operable to allow manually switching between a display of one or more of the representative image, the new image and the merged image; and
the processor generates signals for displaying on a display device according to the user interface.

16. A method for generating a display of an image of a patient's internal anatomy in a surgical field during a medical procedure, comprising:
acquiring an image of the surgical field with the imaging device in a first orientation;
displaying the acquired image;
moving the imaging device, patient, or table from the first orientation;
tracking the movement of the imaging device, patient, or table from the first orientation;
moving the displayed image in relation to the tracked movement prior to acquiring a new image of the surgical field with the imaging device; and
overlaying indicia indicative of a desired movement of the displayed image.

17. The method of claim 16, wherein the indicia is a grid overlaid on the displayed image that remains stationary relative to the displayed image as the displayed images moves.

18. The method of claim 17, wherein the indicia includes a trajectory indicator indicative of the direction of view for the new image that moves with the displayed image.

19. The method of claim 18, wherein the imaging device is moved until the trajectory indicator is aligned with part of the grid prior to acquiring the new image.

20. The method of claim 16, further comprising the step of overlaying identifiers corresponding to the anatomic features in the displayed image that move with the displayed image.

21. The method of claim 16, in which the medical procedure is a surgical navigation procedure in which the position of an object, such as a tool or instrument, is tracked, wherein the new image includes an image of the tool or instrument; and the method further comprises:
introducing a representation of the object on the acquired image;
after moving the displayed image in relation to the tracked movement, acquiring position data corresponding to the tracked position of the object and comparing the position data with the position of the object on the moved image; and
recalibrating the moved image based on the comparison of the position data with the position of the object on the moved image.

22. A method for generating a display of an image of a patient's internal anatomy in a surgical field during a medical procedure, in which the medical procedure includes tools, instruments, implants or other objects that block or obscure the internal anatomy in an image of the surgical field, comprising:
acquiring a high resolution baseline image of anatomy within the surgical field in a baseline orientation;
digitally manipulating the high resolution baseline image to produce a baseline image set including representative images of the baseline image at a plurality of permutations of movements of the baseline image from the baseline orientation;
acquiring a new image of the surgical field in which portions of the anatomy are blocked by objects;
comparing the new image to the representative images in the baseline image set to select a representative image having an acceptable degree of correlation with the new image; and
displaying the selected representative image to show the surgical field minimizing or eliminating the blocking objects.

23. The method of claim 22, wherein the step of comparing the new image to the representative images of the baseline image set includes only comparing portions of the images outside the portions that are blocked or obscured.

24. The method of claim 23, wherein the locations of the blocked or obscured portions of the new image are determined by determining which pixels have a value outside a pre-determined threshold.

* * * * *